(12) United States Patent
Scuderi

(10) Patent No.: US 7,709,215 B2
(45) Date of Patent: May 4, 2010

(54) METHOD FOR DIAGNOSING AND TREATING ACUTE JOINT INJURY

(75) Inventor: Gaetano J. Scuderi, Jupiter, FL (US)

(73) Assignee: Cytonics Corporation, Jupiter, FL (US)

( * ) Notice: Subject to any disclaimer, the term of this patent is extended or adjusted under 35 U.S.C. 154(b) by 0 days.

(21) Appl. No.: 11/809,551

(22) Filed: Jun. 1, 2007

(65) Prior Publication Data

US 2008/0299110 A1 Dec. 4, 2008

(51) Int. Cl.
G01N 33/53 (2006.01)
(52) U.S. Cl. .................................. 435/7.1; 436/536
(58) Field of Classification Search ................ None
See application file for complete search history.

(56) References Cited

U.S. PATENT DOCUMENTS

| | | | |
|---|---|---|---|
| 4,391,904 A | 7/1983 | Liman | |
| 5,225,539 A | 7/1993 | Winter | |
| 5,364,793 A | 11/1994 | Cameron et al. | |
| 5,530,101 A | 6/1996 | Queen | |
| 5,585,089 A | 12/1996 | Queen | |
| 5,693,761 A | 12/1997 | Queen | |
| 5,693,762 A | 12/1997 | Queen | |
| 5,844,097 A | 12/1998 | Cameron et al. | |
| 5,866,007 A | 2/1999 | Whitson | |
| 6,190,691 B1 | 2/2001 | Mak | |
| 6,267,722 B1 | 7/2001 | Anderson | |
| 6,329,511 B1 | 12/2001 | Vasquez | |
| 6,419,944 B2 | 7/2002 | Tobinick et al. | |
| 6,537,549 B2 | 3/2003 | Tobinick | |
| 6,635,250 B2 | 10/2003 | Olmarker et al. | |
| 6,649,589 B1 | 11/2003 | Olmarker et al. | |
| 6,656,745 B1 | 12/2003 | Cole | |
| 6,818,455 B2 | 11/2004 | May | |
| 6,982,089 B2 | 1/2006 | Tobinick | |
| 7,115,557 B2 | 10/2006 | Olmarker | |
| 7,183,390 B2 | 2/2007 | Vasquez | |
| 7,189,522 B2 | 3/2007 | Esfandiari | |
| 2003/0096705 A1 | 5/2003 | Laborde | |
| 2003/0138404 A1 | 7/2003 | Maroun | |
| 2004/0087558 A1 | 5/2004 | Zeldis et al. | |
| 2004/0087931 A1 | 5/2004 | Marsh et al. | |
| 2004/0209307 A1 | 10/2004 | Valkirs et al. | |
| 2005/0025765 A1 | 2/2005 | DiMauro et al. | |
| 2005/0038001 A1 | 2/2005 | Attawia et al. | |
| 2005/0152905 A1 | 7/2005 | Omoigui | |
| 2006/0046961 A1 | 3/2006 | McKay et al. | |
| 2006/0051381 A1 | 3/2006 | Tobinick | |
| 2006/0094056 A1 | 5/2006 | Chappelle et al. | |
| 2006/0165696 A1 | 7/2006 | Okano et al. | |
| 2006/0251653 A1 | 11/2006 | Okuda | |
| 2007/0122405 A1 | 5/2007 | Roschke | |
| 2008/0015465 A1 | 1/2008 | Scuderi et al. | |

FOREIGN PATENT DOCUMENTS

| | | |
|---|---|---|
| WO | WO 90/07861 | 7/1990 |
| WO | WO 91/17271 | 11/1991 |
| WO | WO 92/01047 | 1/1992 |
| WO | WO 93/12227 | 6/1993 |
| WO | WO 2005/018431 | 3/2005 |
| WO | WO 2007/147140 | 12/2007 |

OTHER PUBLICATIONS

Lamana et al. (2006). Eur. J. Immuno. vol. 36, No. 10, pp. 2632-2638.*
Akerstrom, et al., "Protein G: a powerful tool for binding and detection of monoclonal and polyclonal antibodies", *J. Immunol.*, 135(4):2589-92 (1985).
Boye, et al., "An overview of the current clinical use of the anti-CD20 monoclonal antibody rituximab", *Ann. Oncol.*, 14(4):520-35 (2003).
Cocchi, et al., "Identification of RANTES, MIP-1 alpha, and MIP-1 beta as the major HIV-suppressive factors produced by CD8+T cells", *Science*, 270(5243):1811-5 (1995).
Corrigall, et al., "Functional IL-2 receptor beta (CD122) and gamma (CD132) chains are expressed by fibroblast-like synoviocytes: activation by IL-2 stimulates monocyte chemoattractant protein-1 production", *J. Immunol.*, 166(6):4141-7 (2001).
Hirano, et al., "Complementary DNA for a novel human interleukin (BSF-2) that induces B lymphocytes to produce immunoglobulin", *Nature*, 324(6092):73-6 (1986).
Huse, et al., "Generation of a large combinatorial library of the immunoglobulin repertoire in phage lambda", *Science*, 246(4935):1275-81 (1989).
Isaacs, et al., "Virus interference. II. Some properties of interferon.", *Proc. R. Soc. Lond. B Biol. Sci.*, 147(927):268-73 (1957).

(Continued)

Primary Examiner—Prema Mertz
(74) Attorney, Agent, or Firm—Pabst Patent Group LLP

(57) ABSTRACT

The present invention provides methods, reagents and kits for diagnosing and/or for the prognosis of non-autoimmune acute joint inflammation by detecting cytokine biomarkers in a sample obtained from an individual thought to be suffering from joint injury. The cytokine biomarkers used with the methods and kits of the present invention are IL-6, MIP-1β, MCP1 and IFNγ.

8 Claims, 2 Drawing Sheets

OTHER PUBLICATIONS

Kamin-Lewis, et al., "Perforin-low memory CD8+ cells are the predominant T cells in normal humans that synthesize the beta-chemokine macrophage inflammatory protein-1beta", *Proc. Natl. Acad. Sci. U.S.A.*, 98(16):9283-8 (2001).

Kronval, "A surface component in group A, C, and G streptococci with non-immune reactivity for immunoglobulin G", *J. Immunol.*, 111(5):1401-6 (1973).

McCafferty, et al., "Phage antibodies: filamentous phage displaying antibody variable domains", *Nature*, 348(6301):552-4.

Modi, et al., "The human MIP-1beta chemokine is encoded by two paralogous genes, ACT-2 and LAG-1", *Immunogenetics*, 53(7):543-9 (2001).

Moseley, et al., "A controlled trial of arthroscopic surgery for osteoarthritis of the knee", *N. Engl. J. Med.*, 347(2):81-8 (2002).

Queen, et al., "A humanized antibody that binds to the interleukin 2 receptor", *Proc. Natl. Acad. Sci. U.S.A.*, 86(24):10029-33 (1989).

Sehgal, et al., "Human beta 2 interferon and B-cell differentiation factor BSF-2 are identical", *Science*, 235(4790):731-2 (1987).

Takayanagi, et al., "T-cell-mediated regulation of osteoclastogenesis by signalling cross-talk between RANKL and IFN-gamma", *Nature*, 408(6812):600-5 (2000).

Ward, et al., "Binding activities of a repertoire of single immunoglobulin variable domains secreted from *Escherichia coli*", *Nature*, 341(6242):544-6 (1989).

Mulleman, et al., "Pathophysiology of disk-related low back pain and sciatica. II. Evidence supporting treatment with TNF-alpha antagonists", *Joint Bone Spine*, 73(3):270-7 (2006). Epub Jun. 22, 2005.

Park, et al., "The pattern of interleukin-12 and T-helper types 1 and 2 cytokine expression in herniated lumbar disc tissue", *Spine*, 27(19):2125-8 (2002).

Zanetti, et al. "Patients with suspected meniscal tears: prevalence of abnormalities seen on MRI of 100 symptomatic and 100 contralateral asymptomatic knees", *AJR Am J Roentgenol.* 181(3):635-41 (2003).

Scuderi, et al. "Cytokine assay of the epidural space lavage in patients with lumbar intervertebral disk herniation and radiculopathy", *J. Spinal Disord. Tech.*, 19(4):266-9 (2006).

* cited by examiner

METHOD FOR DIAGNOSING AND TREATING ACUTE JOINT INJURY

CROSS-REFERENCES TO RELATED APPLICATIONS

Not applicable

STATEMENT AS TO RIGHTS TO INVENTIONS MADE UNDER FEDERALLY SPONSORED RESEARCH AND DEVELOPMENT

Not applicable

REFERENCE TO A "SEQUENCE LISTING," A TABLE, OR A COMPUTER PROGRAM LISTING APPENDIX SUBMITTED ON A COMPACT DISK

Not applicable

BACKGROUND OF THE INVENTION

Increasing degrees of force applied to joints result in joint injury. Abnormal joint anatomy is frequently a hallmark of ageing, but joint injury is also frequently seen as a result of trauma. For instance, chondral lesions are often seen in athletes. While joint injury resulting from trauma is typically associated with acute inflammation, aberrant joint anatomy resulting from ageing (e.g., osteoarthritis) is a chronic condition. Physicians currently do not have a system or method available to differentiate between acute injury due to trauma and age related joint deteriorations. It is presently difficult to determine the appropriate course of treatment for a given patient since it is frequently unclear whether the particular condition the patient suffers from is acute or chronic.

The exceedingly high rate of exploratory knee arthroscopy highlights the difficulty of diagnosing meniscal injury. This problem is exacerbated by the low specificity of MRI, currently a mainstay of diagnosing this pathology. It has been shown that MRI will identify a meniscal injury in as many as 65% of asymptomatic people making MRI a questionable diagnostic tool and highlighting the lack of correlation between abnormal meniscal anatomy and knee pain. Lack of a clear correlation between abnormal meniscus anatomy and knee pain is particularly problematic in the elderly patient population many of whom develop osteoarthritis. Despite the overwhelming evidence questioning its utility (Moseley et al. 2002), knee arthroscopy is still performed an estimated 660,000 times per year in the U.S. alone (AAOS website).

There is clearly a need for providing a method of identifying patients who have sustained acute joint injury in order to provide them with the appropriate treatment. This invention addresses that need.

BRIEF SUMMARY OF THE INVENTION

The present invention provides methods, kits and reagents for selecting patients with acute non-autoimmune joint injury for treatment. In some embodiments, the present invention provides a method of selecting a patient for treatment, wherein the patient is suffering from non-autoimmune acute joint pain, the method comprising: detecting the level of IL-6 in a biological sample from a joint, wherein the presence of IL-6 is indicative of a patient to be selected for treatment. In some embodiments, the methods of the present invention further comprise detecting the level in the biological sample from the joint of at least one other cytokine selected from the group consisting of MCP-1, MIP-1β and IFNγ. In some embodiments, the one other cytokine is MCP-1. In other embodiments, the one other cytokine is MIP-1β. In yet other embodiments, the one other cytokine is IFNγ.

In some embodiments, the biological sample from the joint is a fluid from the joint. In other embodiments, the biological sample from the joint is a lavage sample.

In some embodiments, IL-6 or IL-6 and at least one other cytokine are detected by way of an immunoassay. In some embodiments, IL-6 or IL-6 and at least one other cytokine are detected using a method of detection that comprises detecting the level of nucleic acid. In some embodiments, detecting the nucleic acid can be done using am amplification reaction. In some embodiments, the amplification reaction is a polymerase chain reaction (PCR).

In some embodiments the joint subjected to the methods of the present invention is a synovial joint. In some embodiments, the joint subjected to the methods of the present invention is a knee. In other embodiments, the methods of the present invention can be used on a shoulder. In yet other embodiments, the methods of the present invention are performed on a wrist. In other embodiments, the joint subjected to the methods of the present invention is an elbow. In other embodiments, the joint subjected to the methods of the present invention is a hip. In yet other embodiments, the methods of the present invention can be practiced on the small joints of a hand or a foot.

In some embodiments, the methods of the present invention further comprise treating the patient. In some embodiments, the patient can be treated surgically. In other embodiments, a treatment agent can be administered to the patient. In some embodiments the treatment agent administered to the patient can be an anti-inflammatory agent.

In some embodiments, the present invention provides a method of selecting a patient for treatment, wherein the patient is suffering from non-autoimmune acute pain of a joint, the method comprising: detecting the level of MCP-1 in a biological sample from a joint, wherein the presence of MCP-1 is indicative of a patient to be selected for treatment. In some embodiments, the method of the present invention further comprises detecting the level of at least one other cytokine selected from the group consisting of IL-6, MIP-1β and IFNγ. In some embodiments, MCP-1 and IL-6 are detected. In some embodiments, MCP-1 and MIP-1β are detected. In some embodiments, IL-6 and IFNγ are detected. In some embodiments, prediction of success of surgery can also be determined based on the diagnostic presence of the cytokine biomarkers of the present invention. For example, a patients with elevated IL-6 or MCP1 levels is more likely to have beneficial outcome from surgical treatment.

In some embodiments, MCP-1 alone or MCP-1 and at least one other cytokine from the group consisting of IL-6, MIP-1β and IFNγ is detected in a fluid from a joint. In other embodiments, MCP-1 alone or MCP-1 and at least one other cytokine from the group consisting of IL-6, MIP-1β and IFNγ is(are) detected in a lavage sample from a joint.

In some embodiments MCP-1 alone or MCP-1 and at least one other cytokine from the group consisting of IL-6, MIP-1β and IFNγ is(are) detected in an immunoassay. In other embodiments, the nucleic acid coding for MCP-1 or MCP-1 and at least one other cytokine from the group consisting of IL-6, MIP-1β and IFNγ is detected in the detection method. In some embodiments, the nucleic acid is detected using an amplification reaction. In some embodiments, the amplification reaction used as a method of detection is a polymerase chain reaction (PCR).

The methods of the present invention can be practiced on a joint sample from any synovial joint. In some embodiments, the joint is selected from the group consisting of knee, wrist, ankle, hip, elbow and shoulder.

In some embodiments, the methods of the present invention further comprise treating the patient. In some embodiments, the patient can be treated surgically. In other embodiments, the patient can be treated with an anti-inflammatory agent. For example, the patient can be treated with an inhibitor of IL-6, MCP-1, INFγ and/or MIP-1β such as an antibody.

The present invention provides a kit comprising an antibody panel, wherein the antibody panel consists of an antibody to IL-6 and one or more antibodies to a cytokine selected from the group of MCP-1, INFγ and MIP-1β. In some embodiment, the antibody panel consists of an antibody to IL-6 and an antibody to MCP1. In some embodiments, the antibody panel consists of an antibody to IL-6, an antibody to MCP-1 and either an antibody to IFNγ or an antibody to MIP-1β. In some embodiment, the antibody panel consists of an antibody to IL-6, an antibody to MCP-1, an antibody to IFNγ and an antibody to MIP-1β. In some embodiments, the antibodies in the kit are on a continuous solid substrate. In other embodiments, the antibodies in the kit are each provided on a separate solid surface. In some embodiments, the kit further provides a device for extracting the biological sample from a joint. In some embodiments, the extraction device provided in the kit is directly linked to a chamber comprising the antibody panel.

DETAILED DESCRIPTION OF THE INVENTION

I. Definitions

Figure 1:
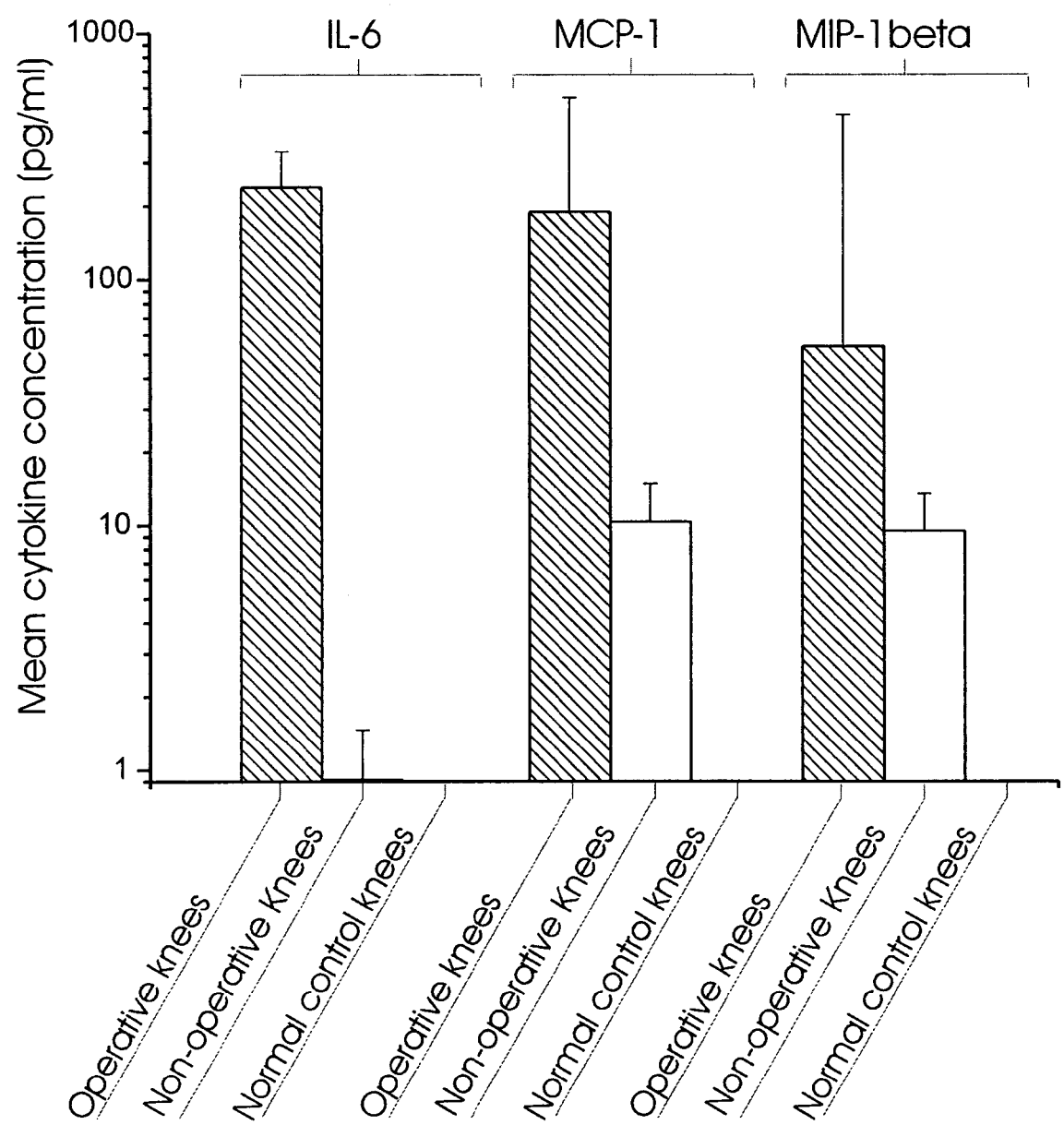
FIG. 1 depicts a comparison of the mean concentration levels of IL-6, MCP-1 and MIP-1beta in operative knees, non-operative knees and normal control knees.
Figure 2:
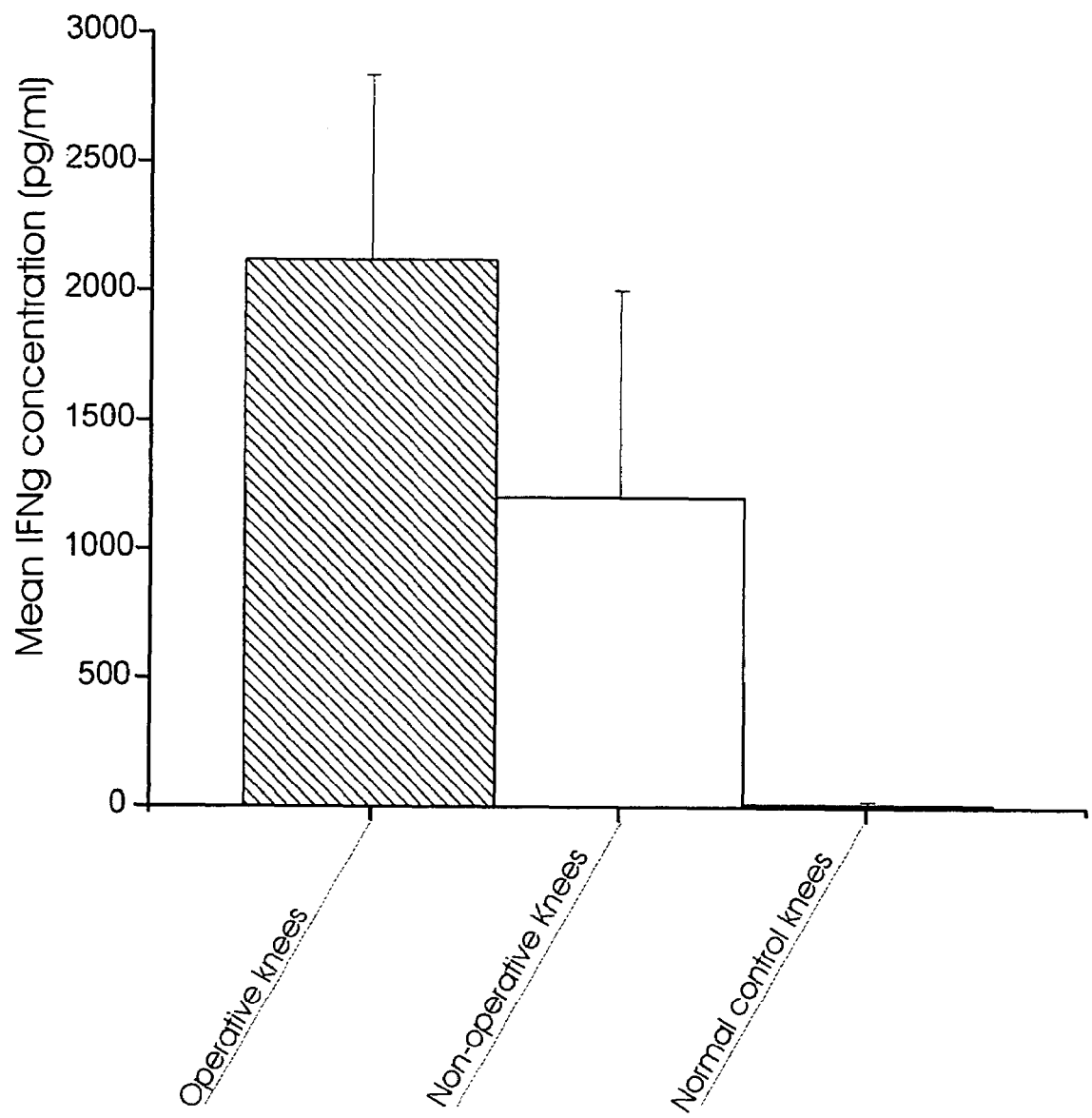
FIG. 2 depicts a comparison of mean IFNγ levels in operative knees, non-operative knees and normal control knees. An operative knee is defined as a knee a physician deems requires surgical rectification. A non-operative knee is a contralateral side to an operated knee.

As used herein "acute pain" or "acute inflammation of the joint" or "acute joint inflammation" or "acute joint injury (lesion)" or "acute chondral injury (lesion) "acute meniscal injury (lesion)" is used to refer to joint or chondral or cartilaginous or meniscal injury associated with pain for about 30 weeks or less. The term "acute" is used to differentiate such pain or inflammation from chronic disorders such as osteoarthritis or any other type of chronic disorder. A chronic disorder is a disorder associated with periods of pain longer than about 30 weeks or any damage to the joint that is associated with general, age-related deterioration of the joint.

The term "joint deterioration" or "abnormal meniscal/chondral/joint anatomy" is used herein to refer to any abnormalities in the anatomy of the joint that can be visualized on an MRI and that are typically associated with the typical joint deterioration as a result of ageing.

"Patient" refers to humans, other non-human primates and other mammals. Typically, a patient is a human. In some instances, the patient is simian, feline, canine, equine, porcine, bovine, ovine or caprine.

The term "joint" as used herein refers to any diarthoidal (also called synovial) joints. The term "joint" thus refers to any joint containing bone, articular cartilage, a joint capsule, a synovial tissue lining, and lubricating synovial fluid inside the capsule. The term "chondral" refers to the cartilage components of a joint. Typically, the term "meniscal" refers to a component of the knee. In some embodiments, the synovial joint is used here to refer to a shoulder or wrist or ankle or hip or elbow, or the small joints of the fingers or toes.

The term "biological sample" refers to a cell or population of cells or a quantity of tissue, fluid or lavasate from the joint of a subject. A biological sample can comprise cells from cartilagenous tissue or can be free of cells.

The term "non-autoimmune" as used herein when referring to acute joint inflammation is used to describe an inflammatory response or reaction that does not involve self-reactive antibodies. Rheumatoid arthritis is an example of autoimmune condition characterized by joint inflammation.

The term "antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. The singular term "an antibody" as used herein is understood to encompass plural referents unless the context clearly indicates otherwise. In some instances the plurality of the antibodies can belong to the same antibody species, e.g., in the case of monoclonal antibodies, while in some cases different antibodies species are encompassed the by phrase "an antibody", e.g., a polyclonal antibodies.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H$1 by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)). When referring to treatment methods, antibodies that are chimeric, human, humanized or otherwise specific to the species to be treated are used.

The term "agent" is used to describe a compound that has or may have a pharmacological activity. Agents include compounds that are known drugs, compounds for which pharmacological activity has been identified but that are undergoing further therapeutic evaluation, and compounds that are members of collections and libraries that are to be screened for a pharmacological activity. The term includes an organic or inorganic chemical such a peptide, protein, including antibodies, and small molecules and natural products.

A "normal joint" or a "control joint" as used herein typically refers to a joint with an insignificant level of pain. The level of pain that might be present in a normal joint, typically does not impact the function or quality of the patient's life to the degree that the patient seeks medical care. Alternatively a "normal" or "control joint" may be a joint subject to chronic pain lasting over 30 weeks such as, for example, an arthritic joint.

The phrase "cytokine biomarker" or "cytokine marker" as used herein refers to the following cytokines and chemokines: IL-6, MIP-1β, MCP-1 or IFNγ. In some instances, the phrase "cytokine biomarker" or "cytokine marker" refers to a polypeptide fragment of IL-6, MIP-1β, MCP-1 or IFNγ. "Diagnostic levels" of cytokine biomarkers as used herein refer to the presence of levels of IL-6, IFNγ, MCP-1 or MIP-1β that are statistically significantly elevated relative to a normal joint. In some instances, IL-6 alone is used as a diagnostic marker. In some instances, MCP-1 alone is used as a diagnostic biomarker. In some other instances, IFNγ alone is used as a diagnostic marker. In some instances, MIP-1β alone is used as a diagnostic marker. In other embodiments, the presence or levels of IL-6 and any one or more of the other three cytokine biomarkers (MIP-1β or MCP1 or IFNγ) are used as diagnostic biomarkers. In some other embodiments, the presence or levels of MCP-1 and any one or more of the other three cytokine biomarkers (MIP-1β or IL-6 or IFNγ) are used as diagnostic biomarkers. In other embodiments, all four cytokine biomarkers are used in a diagnostic assay.

The term "immunoassay" refers to an assay that uses an antibody or antibodies to specifically bind an antigen. The immunoassay is characterized by the use of specific binding properties of a particular antibody or antibodies to isolate, target, and/or quantify the antigen.

"Specific binding" between a binding agent, e.g., an antibody and a protein, for instance, a biomarker cytokine, refers to the ability of a capture- or detection-agent to preferentially bind to a particular cytokine that is present in a mixture; e.g., a fluid from a joint. Specific binding also means a dissociation constant ($K_D$) that is less than about $10^{-6}$ M; preferably, less than about $10^{-8}$M; and, most preferably, less than about $10^{-9}$ M.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample.

The phrase "level of cytokine biomarker" in a biological sample as used herein typically refers to the amount of protein, protein fragment or peptide levels of the cytokine biomarker (for example, IFNγ or IL-6 or MCP1 or MIP-1β) that is present in a biological sample A "level of cytokine biomarker" need not be quantified, but can simply be detected, e.g., a subjective, visual detection by a human, with or without comparison to a level from a control sample or a level expected of a control sample.

The "level of cytokine biomarker mRNA" in a biological sample as used herein refers to the amount of mRNA encoding the cytokine biomarker (for example, IFNγ or IL-6 or MCP1 or MIP-1β) that is present in a cell or a biological sample. A "level of cytokine biomarker mRNA" need not be quantified, but can simply be detected, e.g., a subjective, visual detection by a human, with or without comparison to a level from a control sample or a level expected of a control sample.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

A "label" or a "detectable moiety" is a composition detectable by spectroscopic, photochemical, biochemical, radiographic, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The labels may be incorporated into nucleic acids, proteins and antibodies at any position. Any method known in the art for conjugating the antibody to the label may be employed, e.g., using methods described in Hermanson, *Bioconjugate Techniques* 1996, Academic Press, Inc., San Diego.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe. Alternatively, method using high affinity interactions may achieve the same results where one of a pair of binding partners binds to the other, e.g., biotin, streptavidin.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not functionally interfere with hybridization. Thus, e.g., probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence. Diagnosis or prognosis may be based at the genomic level, or at the level of RNA or protein expression.

By "determining the functional effect" is meant assaying for a compound that increases or decreases a parameter that is indirectly or directly under the influence of a cytokine biomarker (e.g., IL-6, IFNγ, MCP1 or MIP1β) protein sequence, e.g., functional, enzymatic, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties for the protein, measuring inducible markers or transcriptional activation of the cytokine biomarker protein; measuring binding activity or binding assays, e.g. binding to antibodies or other ligands, and measuring cellular proliferation. Determination of the functional effect of a compound on joint injury can be performed using exemplary assays disclosed above. The functional effects can be evaluated by many means known to those skilled in the art, e.g., microscopy for quantitative or qualitative measures of alterations in morphological features, measurement of changes in RNA or protein levels for cytokine biomarker sequences, measurement of RNA stability, identification of downstream or reporter gene expression, e.g., via chemiluminescence, fluorescence, colorimetric reactions, antibody binding, inducible markers, and ligand binding assays.

"Inhibitors" or "antagonist" or "modulators" of the cytokine biomarker polynucleotide and polypeptide sequences are used herein to refer to molecules of agents capable of inhibiting, inactivating or reducing the levels of the cytokine biomarkers. Inhibitors are compounds that, e.g., bind to, partially or totally block activity, decrease, prevent, delay activation, inactivate, desensitize, or down regulate the activity or expression of cytokine biomarker proteins, e.g., antagonists. Inhibitors include polypeptide inhibitors, such as antibodies, soluble receptors and the like, as well as nucleic acid inhibitors such as siRNA or antisense RNA, genetically modified versions of the cytokine biomarker proteins, e.g., versions with altered activity, as well as naturally occurring and synthetic cytokine biomarker antagonists, small chemical molecules and the like. Assays for detecting inhibitors include, e.g., expressing the cytokine biomarker protein in vitro, in cells, or cell membranes, applying putative antagonist compounds, and then determining the functional effects on cytokine activity, as described above.

II. Introduction

The present invention provides methods, reagents and kits for diagnosing and/or for the prognosis of non-autoimmune acute joint inflammation by detecting biomarkers in a sample obtained from an individual thought to be suffering from acute joint injury. The invention is based on the discovery that the presence and levels of certain biomarker cytokines, e.g., the presence and levels of IL-6 or MCP1 can be used to diagnose acute inflammation of a joint. In some embodiments, IL-6 and at least one other biomarker cytokine selected from the group consisting of MCP-1, MIP-1β and IFNγ can be used to diagnose acute inflammation of a joint. In some embodiments MCP-1 and at least one other biomarker cytokine selected from the group consisting of IL-6, MIP-1β and IFNγ can be used to diagnose acute inflammation of the joint.

The present invention provides methods to detect joint injury or methods for treating joint injury, e.g., by inhibiting the expression and/or activity of one or more of the biomarker cytokines.

The methods of the invention typically involve detecting the presence of the biomarker cytokine(s) in a sample taken from a joint from a patient. In certain embodiments, the levels of the biomarker cytokines will be compared to a control value obtained from a normal, injury free joint of a subject or from a joint from a subject where the joint is not painful. In some embodiments, the control sample can be taken from a non-injured joint of the same subject.

The method of the present invention thus provides a criterion for the determination of acute joint injury in a patient to aid in selecting patients as candidates for treatment and/or surgery. The methods of the present invention provide additional criterions for selecting patients who have sustained joint injury regardless of whether such patients suffer from normal, age-related deterioration of the joint(s).

III. Patient Population

For the purposes of the present invention, patients are individuals who have been suffering from acute joint pain An individual suffering from acute pain is an individual who has been experiencing pain in a joint for 30 or 25 weeks or less. In some embodiments, the patient has been experiencing joint pain for 20 weeks or less. In other embodiments, the patient has been experiencing joint pain for 15 weeks or less. In some embodiments, the patient has been experiencing joint pain for 10 weeks or less. In some embodiments, the patient has been experiencing joint pain for 8 weeks or less. In some embodiments, the patient has been experiencing joint pain for 6 weeks or less. In some embodiments, the patient has been experiencing joint pain for 4 weeks or less. In some embodiments, the patient has been experiencing joint pain for 2 weeks or less. In some embodiments, the patient has been experiencing joint pain for 1 weeks or less. The present invention allows for the differentiation of acute joint pain from chronic joint pain such as pain that is frequently associated with osteoarthritis or rheumatoid arthritis. The methods of the present invention can be practiced on patients regardless of their age and sex.

In some instances, patients are selected based on the pain they experience in the affected joint. In some embodiments patients are selected for cytokine level assessment based on a recent joint injury. A recent join injury indicates an injury that has been associated with pain for about thirty weeks or less.

Candidate patients for the methods of the present invention include patients who experience pain or are suspected to have acute inflammation of a joint. Typically, the methods of the present invention are applicable to human or animal diarthrodial joints. A diarthrodial joint contains a bone, articular cartilage, a joint capsule, synovial tissue lining, and a lubricating synovial fluid inside the capsule. By way of non-limiting example, the methods of the present invention can be applied to a shoulder, a knee, a wrist, an ankle, an elbow, a hip or any of the finger or toe joints.

IV. Detecting Cytokine Biomarkers a) Cytokine Biomarkers

Any one of, or any combination of the following cytokine biomarkers can be used to practice the methods of the present invention: IL-6, IFNγ, MIP-1β and/or MCP1. In some embodiments, the cytokine biomarkers used for the methods of the present invention are IL-6 alone or IL-6 and any combination of the following biomarkers: MCP1, MIP-1β, and IFNγ. In some embodiments, IL-6 and IFNγ are used to practice the methods of the present invention. In some embodiments, IL-6 and MIP-1β are used as the cytokine biomarkers to diagnose acute joint inflammation. In some embodiments, IL-6 and MCP1 are the cytokine biomarkers used to practice the methods of the present invention. In some embodiments, IL-6 and INFγ are used with either of or both MCP1 or MIP-1β to practice the methods of the present invention.

In some embodiments, the cytokine biomarkers used for the methods of the present invention are either MCP-1 alone or MCP-1 and any combination of the following biomarkers: IL-6, MIP-1β, and IFNγ. In some embodiments, MCP-1 and IFNγ are used to practice the methods of the present invention. In some embodiments, MCP-1 and MIP-1β are used as the cytokine biomarkers to diagnose acute joint inflammation. In some embodiments, MCP-1 and IL-6 are the cytokine biomarkers used to practice the methods of the present invention. In some embodiments, MCP-1 and INFγ are used with either of or both IL-6 or MIP-1β to practice the methods of the present invention.

In some embodiments, MIP1β alone is used as a cytokine biomarker of the present invention. In certain embodiments, IFNγ is used as a cytokine biomarker to practice the methods of the present invention.

The biological significance of IL-6 (also called IFN-beta-2) lies in the fact that it is induced under conditions in which IFN-beta-1 is not induced, as in metabolically stressed cells. Its induction by IL1 and TNFα suggests that it may play a role as an autocrine mediator of some effects of these cytokines in inflammation and acute phase responses, as well as regulate cell proliferation. IL-6 is identical to B-cell differentiation factor (BSF2) and enhances proliferation in hybridoma/plasmacytoma cells (Sehgal et al., Science 235: 731-732 (1987)). The primary sequence of IL-6 deduced from the cDNA shows that it has 184 amino acids and is distinct from other interleukins (Hirano et al., Nature 324: 73-76 (1986). In addition to its antiviral activity, IL-6 elicits acute phase response in liver cells. An exemplary human amino acid IL-6 sequence can be found deposited under NCBI accession number NP_000591.

Interferons were originally characterized as antiviral entities (Isaacs et al., Proc. Roy. Soc. London 147B: 268-273 (1957). Two major classes of acid-stable (type I) interferons have been recognized in humans: (1) leukocyte interferon, released by stimulated leukocytes, (2) and fibroblast interferon, produced by stimulated fibroblasts. The two classes of interferons differ not only immunologically but also in their target cell specificities, although both induce a virus-resistant state in human cells. Human interferons have been classified into 3 groups: alpha, beta, and gamma. Both alpha- and beta-IFNs, previously designated type I, are acid-stable, but they differ immunologically and in regard to some biologic and physiochemical properties. The gamma or immune IFNs, which are produced by T lymphocytes in response to mitogens or to antigens to which they are sensitized, are acid-labile and serologically distinct from alpha- and beta-IFNs. An exemplary amino acid sequence for human IFNγ has been deposited under accession number NP_000610.

A variety of functions have been attributed to IFN gamma. For instance, it is well known that IFN gamma is a cytokine integral to the development of the Th1 lineage of T cells. T-cell production of IFNγ strongly suppresses osteoclastogenesis by interfering with the RANKL/RANK signaling pathway (Takayanagi et al., Nature 408: 600-605 (2000)). IFNγ induces rapid degradation of the RANK adaptor protein, TRAF6, resulting in strong inhibition of the RANKL-induced activation of the transcription factor NFκB and JNK. This inhibition of osteoclastogenesis could be rescued by overexpressing TRAF6 in precursor cells, indicating that TRAF6 is the target critical for the IFNγ action. Furthermore, Takayanagi et al. (2000) concluded that there is crosstalk between the tumor necrosis factor (TNF) and IFN families of cytokines, through which IFNγ provides a negative link between T-cell activation and bone resorption (Takayanagi et al., Nature 408: 600-605 (2000)).

MIP1β is an 8-kD acidic protein that is upregulated upon stimulation in monocytes, T cells, and other lymphocytes. It belongs to the CC chemokine subfamily and directs the migration of specific subsets of leukocytes. MI1β is encoded by 2 paralogous genes, ACT2 (CCL4) and LAG1 (CCL4L), that are closely situated on the long arm of chromosome 17 (Modi et al., Immunogenetics 53: 543-549 (2001)). The proteins share a common length and are identical at 89 of 92 amino acids. The first 2 amino acid differences occur in the signal peptide, while the third is in the mature protein. Within the transcribed region, the genes differ at 25 of 662 nucleotides. The amino acid sequence deposited under accession number P13236 is an exemplary sequence for MIP-1β.

Cocchi and colleagues identified RANTES, MIP-1-alpha, and MIP-1-beta as the major HIV-suppressive factors produced by CD8+T cells (Cocchi et al., Science 270: 1811-1815 (1995)).

Predominantly perforin-low memory CD8+T cells normally synthesize MIP-1-beta (Kamin-Lewis et al., Nat. Acad. Sci. 98: 9283-9288 (2001)). This beta-chemokine is clearly synthesized by a major population of CD8+T cells with a phenotype that is not consistent with cytotoxic T-lymphocyte effector function.

Fibroblast-like synoviocytes (FLS) obtained from rheumatoid arthritis and osteoarthritis patients exhibited expression of a functional IL2 receptor of intermediate affinity composed solely of IL2Rβ and IL2Rγ (Corrigall et al., J. Immun. 166: 4141-4147 (2001)). Addition of recombinant IL2, IL1β, or TNFα independently did not upregulate expression of the receptors on FLS, but IL2 or IL1β did significantly increase expression of intracellular tyrosine-phosphorylated proteins and the production of MCP1. MCP1 has been proposed to serve to recruit macrophages and perpetuate inflammation in the joints of patients with rheumatoid arthritis (Corrigall et al., J. Immun. 166: 4141-4147 (2001)). A representative sequence for human MCP1 has been deposited under accession number AAQ75526.

b) Methods for Detecting the Cytokine Biomarkers

In the present invention, presence or levels of any one or any combination of the cytokine biomarkers IL-6, MIP-1β, MCP1 and IFNγ can be used to select a patient with acute joint injury for treatment. In some instances, the cytokine biomarkers, IL-6 or IL-6 and one or more of the following cytokine biomarkers: MIP-1β, MCP1 and IFNγ, can be used to diagnose acute inflammation of a joint. In some instances, the cytokine biomarkers, MCP1 or MCP1 and one or more of the following cytokine biomarkers: MIP-1β, IL-6 and IFNγ, can be used to diagnose acute inflammation of a joint. In some embodiments, the presence or level of these cytokine biomarkers can be used to select a patient as candidate for treatment. In some other embodiments, the presence or levels of the cytokine markers can be used to determine the success during the course of or after treatment of an inflamed joint.

Biological samples in which the cytokine markers can be detected include, for example, fluids from joints. In some embodiments, biological samples include a tissue biopsy which may or may not have a liquid component. In some instances, e.g., when fluid cannot be extracted from the joint, a lavage of the joint may be performed. A lavage involves using a physiologic compatible solution, e.g., saline. Methods for obtaining fluid from joint samples are well known to those of skill in the art. For example, fluid or a lavage sample can be extracted or from a joint using a needle and a syringe. In some embodiments, fluid can be extracted from joint using a flexible device with an absorbent material on the tip. The device can comprise a syringe with saline placed over a flexible sheath; the saline can then be injected and needle removed leaving the sheath behind. An absorbent material, e.g., cotton, at the end of permanent suture material or the end of fixed insertion device can then be inserted through a sheath into the joint. The flexing of the joint at this point can allow the absorbent material to absorb the fluid. The absorbent material can be wet with a physiologic solution, e.g., saline, and upon extraction of the fluid from a joint, the tip of the absorbent material can be then directly applied to a testing strip or testing chamber.

Immunoassays can be used to qualitatively or quantitatively analyze the cytokine biomarker levels, e.g., the levels of IL-6 or MIP-1β or MCP-1 or IFNγ in a biological sample. A general overview of the applicable technology can be found in a number of readily available manuals, e.g., Harlow & Lane, Cold Spring Harbor Laboratory Press, *Using Antibodies: A Laboratory Manual* (1999).

In addition to using immunoassays to detect the levels of cytokines in a fluid sample from a joint, assessment of cytokine expression and levels can be made based on the level of gene expression of the particular cytokines. RNA hybridization techniques for determining the presence and/or level of mRNA expression are well known to those of skill in the art and can be used to assess the presence or level of gene expression of the cytokine biomarkers of interest.

c) Antibodies and Immunoassays

In some embodiments, the methods and kits of the present invention utilize selective binding partners of the cytokine biomakers IL-6, MIP-1β, MCP1 and IFNγ to identify the presence or determine the levels of the cytokine biomarkers in a biological sample. The selective binding partner to be used with the methods and kits of the present invention can be, for instance, an antibody. In some aspects, monoclonal antibodies to the particular cytokine biomarkers can be used. In some other aspects, polyclonal antibodies to the particular cytokine biomarkers can be employed to practice the methods and in the kits of the present invention.

Commercial antibodies to the cytokine biomarkers of the present invention are available and can be used with the methods and kits of the present invention. For example, the RDI division of Fitzgerald Industries Inc (Fitzgerald Industries International, Inc., Concord, Mass.) offers a wide variety of antibodies: an exemplary goat anti-human IL6 antibody is offered under catalog number RDI-IL6abGP1; an exemplary mouse anti-human MIP1β, antibody is sold by USBiological (United States Biological, Swampscott, Mass.) is available for purchase under catalog number M1202-35. A monoclonal anti human IFNγ antibody produced in a mouse host is available from USBiological is available for sale under catalog number 17662-16M1. Anti human MCP1 antibody (polyclonal) from a chicken host is available from USBiological under catalog number M2749-97. These examples are meant to illustrate the availability of commercial antibodies to the cytokine biomarkers of the present invention and are in no way to be limiting. It is well know to those of skill in the art that the type, source and other aspects of an antibody to be used is a consideration to be made in light of the assay in which the antibody is used. In some instances, antibodies that will recognize its antigen target (in this instance an epitope or multiple epitopes from IL6 or MIP1β or MCP1 or IFNγ) on a Western blot might not applicable to an ELISA or ELISpot assay and vice versa.

In some embodiments, the antibodies to be used for the assays of the present invention can be produced using techniques for producing monoclonal or polyclonal antibodies that are well known in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)). Such antibodies can be used for therapeutic and diagnostic applications, e.g., in the treatment and/or detection of any of the specific cytokine-associated diseases or conditions described herein.

A number of a particular cyotkine's comprising immunogens may be used to produce antibodies specifically reactive with that particular cytokine biomarker. For example, a recombinant IL-6 or MIP-1β or MCP-1 or IFNγ or an antigenic fragment thereof, can be isolated using methods well known to those of skill in the art. Recombinant protein can be expressed in eukaryotic or prokaryotic cells. Recombinant protein is the typically used immunogen for the production of monoclonal or polyclonal antibodies. Alternatively, a synthetic peptide derived from the known sequences of the cytokine biomarkers and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Once IL-6 or MIP-1β or MCP-1 or IFNγ specific antibodies are available, each specific cytokine biomarker can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

Immunological binding assays (or immunoassays) typically use an antibody that specifically binds to a protein or antigen of choice (in this case IL-6 or IFNγ or MIP-1β or MCP-1 or antigenic subsequence thereof). As described above, the antibody (e.g., anti-IL-6, or anti-MIP-1β or anti-MCP-1 or anti-IFNγ) may be produced by any of a number of means well known to those of skill in the art and as described above.

Specific binding of a cytokine to an antibody may typically require an antibody that is selected for its specificity for a particular protein. For example, polyclonal antibodies raised to a particular cytokine (e.g., IL-6 or MIP-1β or MCP-1 or IFNγ) can be selected to obtain only those polyclonal antibodies that are specifically immunoreactive with a particular cytokine (e.g., IL-6 or MIP-1β or MCP-1 or IFNγ), and not with other proteins, except for polymorphic variants, orthologs, and alleles of the particular cytokine. This selection may be achieved by subtracting out antibodies which react with the cytokine of interest. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically the signal of a specific or selective reaction will be at least twice background signal or noise and more typically more than 10 to 100 times background. Antibodies that react only with a particular cytokine ortholog, e.g., from specific species such as rat, mouse, or human, can also be detected as described above, by subtracting out antibodies that bind to the same cytokine from another species.

Immunoassays also often use a labeling agent to specifically bind to and allow for the detection of the complex formed by the antibody and antigen. The labeling agent may itself be one of the moieties comprising the antibody/antigen complex. Thus, the labeling agent may be a labeled anti-IL-6 or anti-MIP1β or anti-MCP-1 or anti-IFNγ antibody. Alternatively, the labeling agent may be a third moiety, such a secondary antibody, that specifically binds to the antibody/cytokine complex (a secondary antibody is typically specific to antibodies of the species from which the first antibody is derived). Other proteins capable of specifically binding immunoglobulin constant regions, such as protein A or protein G may also be used as the label agent. These proteins exhibit a strong affinity for immunoglobulin constant regions from a variety of species (see, e.g., Kronval et al., *J. Immunol.* 111:1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C. In some embodiments, the immunological assay is instantaneous and a read-out for the presence or levels of the cytokine biomarkers is available nearly immediately upon extracting the sample from the acutely painful joint and performing the immunoassay.

Immunoassays for detecting the cytokine biomarkers in samples may be either competitive or noncompetitive.

Noncompetitive immunoassays are assays in which the amount of antigen is directly measured. In one preferred "sandwich" assay, for example, the anti-IL-6 or anti-MIP1β or anti-MCP-1 or anti-IFNγ antibodies can be bound directly to a solid substrate on which they are immobilized. These immobilized antibodies then capture the corresponding cytokine present in the test sample. The cytokine is thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

In competitive assays, the amount of cytokine biomarker, e.g., IL-6 (IL-6 is used as an illustrative example in this description, a similar scenario can be applied to any of the other cytokine biomarkers) present in the sample is measured indirectly by measuring the amount of a known, added (exogenous) cytokine displaced (competed away) from an anti-IL-6 antibody by the unknown IL-6 present in a sample. In one competitive assay, a known amount of IL-6 is added to a sample and the sample is then contacted with an antibody that specifically binds to the IL-6. The amount of exogenous IL-6 bound to the antibody is inversely proportional to the concentration of IL-6 present in the sample. In one embodiment, the antibody is immobilized on a solid substrate. The amount of IL-6 bound to the antibody may be determined either by measuring the amount of IL-6 present in a IL-6/antibody complex, or alternatively by measuring the amount of remaining uncomplexed protein. The amount of IL-6 may be detected by providing a labeled IL-6 molecule.

A hapten inhibition assay is another competitive assay. In this assay the known cytokine, e.g., IFNγ, (IFNγ is used for purposes of illustration of how a hapten inhibition assay works, any of the other cytokines can be similarly used in such an assay) is immobilized on a solid substrate. A known amount of anti-IFNγ antibody is added to the sample, and the sample is then contacted with the immobilized IFNγ. The amount of anti-IFNγ antibody bound to the known immobilized IFNγ is inversely proportional to the amount of IFNγ-present in the sample. As in the embodiment described above, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred. In addition to, or in place of proteinaceos material, various detergents can be incorporated into the immunoassay to minimize non-specific interactions.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, radiographic, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize the cytokine biomarkers, or secondary antibodies that recognize the antibodies to the cytokine biomakers.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Detection methods employing immunoassays are particularly suitable for practice at the point of patient care. Such methods allow for immediate diagnosis and/or prognostic evaluation of the patient. Point of care diagnostic systems are described, e.g., in U.S. Pat. No. 6,267,722 which is incorporated herein by reference. Other immunoassay formats are also available such that an evaluation of the biological sample can be performed without having to send the sample to a laboratory for evaluation. Typically these assays are formatted as solid assays where a reagent, e.g., an antibody is used to detect the cytokine. Exemplary test devices suitable for use with immunoassays such as assays of the present invention are described, for example, in U.S. Pat. Nos. 7,189,522; 6,818,455 and 6,656,745.

d) Detection of Polynucleotides

In some aspects, the present invention provides methods for detection of polynucleotide sequences which code for the cytokine biomarkers (e.g., IL-6, MIP-1β MCP1 and IFNγ) in a biological sample, e.g., for the diagnosis of acute joint injury. As noted above, a "biological sample" refers to a cell or population of cells or a quantity of tissue or fluid from a patient. Most often, the sample has been removed from a patient, but the term "biological sample" can also refer to cells or tissue analyzed in vivo, i.e., without removal from the patient. Typically, a "biological sample" will contain cells from the patient, but the term can also refer to noncellular biological material, such as noncellular fractions of the fluid from a potentially affected joint.

Amplification-based Assays

In one embodiment, amplification-based assays are used to measure the level of IL-6, or MIP-1, or MCP1, or IFNγ. In such an assay, the IL-6, or MIP-1β, or MCP1, or IFNγ nucleic acid sequences act as a template in an amplification reaction (e.g., Polymerase Chain Reaction, or PCR). In a quantitative amplification, the amount of amplification product will be proportional to the amount of template in the original sample. Comparison to appropriate controls provides a measure of the copy number of the cytokine biomarker associated gene. Methods of quantitative amplification are well known to those of skill in the art. Detailed protocols for quantitative PCR are provided, e.g., in Innis et al. (1990) *PCR Protocols, A Guide to Methods and Applications*, Academic Press, Inc. N.Y.). RT-PCR methods are well known to those of skill (see, e.g., Ausubel et al., supra). In some embodiments, quantitative RT-PCR, e.g., a TaqMan® assay, is used, thereby allowing the comparison of the level of mRNA in a sample with a control sample or value. The known nucleic acid sequences for IL-6, MIP-1β, MCP1 and IFNγ are sufficient to enable one of skill to routinely select primers to amplify any portion of the gene. Suitable primers for amplification of specific sequences can be designed using principles well known in the art (see, e.g., Dieffenfach & Dveksler, *PCR Primer: A Laboratory Manual* (1995)).

In some embodiments, a TaqMan® based assay is used to quantify the cytokine biomaker-associated polynucleotides. TaqMan® based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, e.g., AmpliTaq®, results in the cleavage of the TaqMan® probe. This cleavage separates the 5' fluorescent dye and the 3' quenching agent, thereby resulting in an increase in fluorescence as a function of amplification (see, for example, literature provided by Perkin-Elmer, e.g., www2.perkin-elmer.com).

In some embodiments, hybridization based assays can be used to detect the amount of IL-6, or MIP-1β, or MCP1, or IFNγ in the cells of a biological sample. Such assays include dot blot analysis of RNA as well as other assays, e.g., fluorescent in situ hybridization, which is performed on samples that comprise cells. Other hybridization assays are readily available in the art.

V. Diagnosis

The present methods can be used in the diagnosis, prognosis and treatment of acute joint inflammation. In some embodiments the acute inflammation is in the knee, shoulder, elbow, wrist or ankle. Acute inflammation of the joint at any stage during the 30 week period from the onset of pain can be diagnosed using the methods of the present invention.

In numerous embodiments of the present invention, the level and/or presence of IL-6 or MIP-1β or MCP-1 or IFNγ polynucleotide or polypeptide will be detected in a biological sample, thereby detecting the presence or absence of acute inflammation in the biological sample. In some embodiments, the biological sample will comprise a tissue sample from a tissue suspected of being subject to acute inflammation, e.g., a fluid sample or lavasate of a joint.

In some embodiments, a joint sample determined to contain the cytokine biomarkers of the present invention, e.g., a knee fluid sample shown to contain IL-6 and or MCP-1 or a knee sample shown to contain IL-6 and MCP-1 and MIP-1β or a knee sample shown to contain IL-6 and MCP-1 and IFNγ, will be analyzed for IL-6, MCP-1, MIP1β and/or IFNγ levels to further characterize the injured joint, e.g., the efficacy of certain treatments.

The amount of IL-6, MCP-1, IFNγ and/or MIP-1β polynucleotide or polypeptide that will indicate the presence of a acute inflammation and classify the patient as candidate for treatment will depend on numerous factors, including the affected joint, the age, sex, medical history, etc., of the patient, the cell type, the assay format, etc. In some embodiments, a level of IL-6, MCP-1, IFNγ and/or MIP-1β in a biological sample will not be quantified or directly compared with a control sample, but will rather be detected relative to a "diagnostic presence" of IL-6, MCP-1, IFNγ and/or MIP-1β wherein a "diagnostic presence" refers to an amount of IL-6, MCP-1, IFNγ and/or MIP-1β polynucleotide or polypeptide that indicates the presence or likelihood of acute inflammation in the joint of the mammal from which the sample was taken. In some embodiments, a "diagnostic presence" will be detectable in a simple assay giving a positive or negative result, where a positive "detection" of a "diagnostic presence" of IL-6, MCP-1, IFNγ and/or MIP-1β polynucleotide or polypeptide indicates the presence of acute joint inflammation in the mammal.

The IL-6, MCP-1, IFNγ and/or MIP-1β level need not be quantified for a "diagnostic presence" to be detected. Rather any method of determining whether IL-6, MCP-1, IFNγ and/or MIP-1β is present at levels higher than in a normal or control, pain-free joint, sample, or patient may be used. In addition, a "diagnostic presence" does not refer to any absolute quantity of IL-6, MCP-1, IFNγ and/or MIP-1β, but rather on an amount that, depending on the biological sample, assay conditions, medical condition of the mammal, etc., is sufficient to distinguish the level in an acutely inflamed joint sample from a joint sample from a normal or control patient.

Such methods can be practiced regardless of whether any IL-6, MCP-1, IFNγ and/or MIP-1β polynucleotide or polypeptide is normally present, or "expected" to be present, in a particular control sample. For example, IL-6, MCP-1, IFNγ and/or MIP-1β may not be expressed in certain normal joints, resulting in a complete absence of IL-6, MCP-1, IFNγand/or MIP-1β in a control biological sample from such a joint. For such biological samples, a "diagnostic presence" refers to any detectable amount of IL-6, MCP-1, IFNγ and/or MIP-1β, using any assay. In other tissues, however, there may be a detectable level of IL-6, MCP-1, IFNγ and/or MIP-1β present in normal or control joints and a "diagnostic presence" represents a level that is higher than the normal level, preferably representing a "statistically significant" increase over the normal level. Often, a "diagnostic presence" of IL-6, MCP-1, IFNγ and/or MIP-1β polynucleotide, polypeptide, and/or protein activity in a biological sample will be at least about 1.5, 2, 5, 10, 100, 200, 500, 1000 or more fold greater than a level expected in a sample taken from a normal patient or from the normal contralateral joint of the same patient. In some embodiments, the "diagnostic presence" of IL-6, MCP-1, IFNγ and/or MIP-1β polynucleotide, polypeptide, and/or protein activity in a biological sample will be dependent on the specific type of joint. For example, when evaluating the diagnostic presence of a cytokine in the knee vs. the diagnostic presence of a cytokine in the shoulder different levels of the particular cytokine biomarker may be indicative of an acutely inflamed joint. In some embodiments, the diagnostic presence of the cytokine biomarker will depend on the age of the patient. For instance, older patient's knees are frequently affected by arthritic conditions and the fold difference in cytokine levels between the contralateral normal, arthritic knee and the acutely inflamed knee, e.g., due to recent trauma, might be lower than the difference in a patient from a younger age group. In some embodiments, the difference in cytokine biomarker levels between the control knee and the affected knee in the older patient population will be at least about 1.5, 2, 5, 10, 100, 200, 500, 1000 fold. In some embodiments other diagnostic methods including radiograph can be combined with the methods of the present invention to diagnose acute inflammation in a joint.

The presence or level of IL-6, MCP-1, IFNγ and/or MIP-1β or polypeptide fragments thereof can be used to designate a patient as candidate for treatment. The type of treatment, e.g., anti-inflammatory agent or surgery, can be then tailored to severity of the condition as determined by the presence or level of the cytokine biomarkers.

The present methods can also be used to assess the efficacy of a course of treatment. For example, in a mammal with acute joint injury found to contain an elevated amount of IL-6, MCP-1, IFNγ and/or MIP-1β polynucleotide or polypeptide or fragment thereof, the efficacy of an anti-inflammatory treatment can be assessed by monitoring, over time, IL-6, MCP-1, IFNγ and/or MIP-1β levels. For example, a reduction in IL-6, MCP-1, IFNγ and/or MIP-1β polynucleotide or polypeptide levels in a biological sample taken from a mammal following a treatment, compared to a level in a sample taken from the mammal before, or earlier in, the treatment, indicates efficacious treatment.

The methods detecting acute joint inflammation can comprise the detection of one or more cytokine biomarker polynucleotide, polypeptide or polypeptide fragment sequences. Accordingly, IL-6, MCP-1, IFNγ and/or MIP-1β can be used either alone or in any combination for the diagnosis or prognosis acute joint inflammation.

VI. Treatment Methods

In some aspects, the patient selected for treatment is treated by surgically correcting the abnormalities in the affected joint. In some embodiments, treatment methods to ameliorate production of inflammatory cytokines are employed. Such treatment methods include, for example, surgical debridement including open or arthroscopic meniscectomy, or labral debridement in the shoulder. In some instances surgical procedures to remove loose bodies, cartilage or meniscal repair, ligament alignment or synovectomy can be used. In some embodiments, bony realigning procedures of an extra articular nature that may assist in the removal of eccentric strain and pressure forces on a joint, may be employed.

In some embodiments, treatment agents can be administered to the patient. Treatment agents can include, for example, anti-inflammatory treatment therapies. Non-steroidal anti-inflammatory drugs (NSAID) are well known to those of skill in the art. In some embodiments, the treatment methods can involve an NSAID, e.g., ibuprofen, aspirin or paracetamol. Many steroids, e.g., glucocorticoids, reduce inflammation by binding to cortisol receptors. In some embodiments, steroids are used to treat the acutely inflamed joint diagnosed using the methods of the present invention.

Other treatment regiments can be based on neutralizing the elevated cytokine biomarkers. For example, antagonists of one or more of the cytokines from the group of IL-6, MIP-1β, MCP-1 and IFN-γ can be selected for treatment. Antibodies are an example of a suitable antagonists and include mouse antibodies, chimeric antibodies, humanized antibodies, and human antibodies or fragments thereof. Chimeric antibodies are antibodies whose light and heavy chain genes have been constructed, typically by genetic engineering, from immunoglobulin gene segments belonging to different species (see, e.g., Boyce et al., Annals of Oncology 14:520-535 (2003)). For example, the variable (V) segments of the genes from a mouse monoclonal antibody may be joined to human constant (C) segments. A typical chimeric antibody is thus a hybrid protein consisting of the V or antigen-binding domain from a mouse antibody and the C or effector regions from a human antibody.

Humanized antibodies have variable region framework residues substantially from a human antibody (termed an acceptor antibody) and complementarity determining regions substantially from a mouse-antibody, (referred to as the donor immunoglobulin). See Queen et al., Proc. NatL. Acad. Sci. USA 86:10029-10033 (1989) and WO 90/07861, U.S. Pat. Nos. 5,693,762, 5,693,761, 5,585,089, 5,530,101 and Winter, U.S. Pat. No. 5,225,539. The constant region(s), if present, are also substantially or entirely from a human immunoglobulin. Antibodies can be obtained by conventional hybridoma approaches, phage display (see, e.g., Dower et al., WO 91/17271 and McCafferty et al., WO 92/01047), use of transgenic mice with human immune systems (Lonberg et al., WO93/12227 (1993)), among other sources. Nucleic acids encoding immunoglobulin chains can be obtained from hybridomas or cell lines producing antibodies, or based on immunoglobulin nucleic acid or amino acid sequences in the published literature.

Other antagonists of the biomarker cytokines can also be used for treatment purposes. For example, a class of antagonists that can be used for the purposes of the present invention, are the soluble forms of the receptors for the cytokine biomarkers.

In some embodiments, an IL-6 antagonist is an anti-IL-6 antibody that specifically binds to IL-6. A specific antibody has the ability to inhibit or antagonize the action of IL-6 systemically. In some embodiments, the antibody binds IL-6 and prevents it from interacting with or activating its receptors (e.g. IL-6Rα or IL-6Rβ). In some embodiments, the activity of IL-6 can be antagonized by using an antagonist to the interleukin-6 receptors (IL-6R). U.S. Application number 2006251653 describes methods for treating interleukin-6 related disease and discloses a number of interleukin-6 antagonists including, for example, humanized anti-IL-6R antibodies and chimeric anti-IL-6R antibodies. In some embodiments, an IL-6 or IL-6R derivative can be used to block and antagonize the interaction between IL-6/IL-6R.

In some embodiments, MCP1 antagonists include anti-MCP1 antibodies. Antibodies to MCP1 can function by disrupting the ability of MCP1 to bind its binding partners. Binding partners of MCP1 include CD234, matrix metalloproteinase 1, matrix metalloproteinase 3, matrix metalloproteinase 8, a number of CC chemokine receptors including, e.g., CC chemokine receptor 2 and CC chemokine receptor 5. One of skill in the art can easily design an antagonist for disrupting the interaction between MCP1 and its binding partner by targeting either of the interacting domains. WO05018431 describes a variety of ways to disrupt the interaction between MCP1 and its binding partners, for instance, by using antibodies, or an MCP1 derivative. Alternatively chemical compositions that antagonize the activity of MCP1 can be used. U.S. Application 2003096705 describes compounds which antagonize MCP1 function. In other embodiments, agents that bind to MCP1 binding partners, e.g., antibodies to MCP1 binding partners can be used to block the interaction between MCP1 and its binding partner and inhibit activity.

Similarly to the other cytokine/binding partner interactions described herein, the activity of IFNγ can be antagonized by employing, e.g., an antibody against IFNγ or blocking fragment of IFNγ or its binding partner. In some embodiments, IFNγ antagonists for use in the invention are antibodies that bind IFNγ antibodies, e.g., fontolizumab. Such antibodies can be neutralizing antibodies that block IFNγ activity. Humanized antibodies that bind to IFNγ are described, e.g., in U.S. Pat. Nos. 6,329,511 and 7,183,390. In other embodiments, the antibody indirectly inhibits interferon gamma. IFNγ binding partner include, for example, interferon gamma receptor 1, interferon gamma receptor 2, TNFα and protein disulfide isomerase A3. Antibodies to IFNγ's binding partners can also be used to inhibit the activity of IFNg and thus serve as antagonists of IFNγ. Other interferon antagonists useful for the treatment of interferon-related related diseases are described, for example, in U.S. Application 2003138404.

The function of MIP1β can be antagonized, for example, through the use of anti-MIP1β antibodies. Either blocking MIP-1β or one of its binding partners can function to prevent the activity of MIP1β. Known binding partners of MIP1β are, for example, CC chemokine receptor 3, CC chemokine receptor 5 and CC chemokine receptor 8. Fragments of MIP1β or any of its CC chemokine receptor binding partners can also be used to block productive interaction and thus inhibit or antagonize the activity of MIP1β.

Administering Therapeutics

Inhibitors of IL-6, MCP-1, IFNγ and/or MIP-1β can be administered to a patient for the treatment of acute joint pain. As described in detail below, the inhibitors are administered in any suitable manner, optionally with pharmaceutically acceptable carriers.

The identified inhibitors can be administered to a patient at therapeutically effective doses to treat acute joint injury or prevent further deterioration of the joint due to acute inflammation. The compounds are administered to a patient in an amount sufficient to elicit an effective protective or therapeutic response in the patient. An effective therapeutic response is a response that at least partially arrests or slows the symptoms or complications of the disease. An amount adequate to accomplish this is defined as "therapeutically effective dose." The dose will be determined by the efficacy of the particular IL-6, MCP-1, IFNγ and/or MIP-1β inhibitors employed and the condition of the subject, as well as the body weight or surface area of the area to be treated. The size of the dose also will be determined by the existence, nature, and extent of any adverse effects that accompany the administration of a particular compound or vector in a particular subject.

Toxicity and therapeutic efficacy of such compounds can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects.

The data obtained from cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any compound used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a modulator is from about 1 ng/kg to 10 mg/kg for a typical subject.

Pharmaceutical compositions for use in the present invention can be formulated by standard techniques using one or more physiologically acceptable carriers or excipients. The compounds and their physiologically acceptable salts and solvates can be formulated for administration by any suitable route, including orally and by direct injection into the affected joint. Formulations for the forms of administration suitable with the methods of the present invention are well known to those of skill in the art.

The compounds can be formulated for administration by injection, for example, by bolus injection. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use.

VII. Kits for Use in Diagnostic and/or Prognostic Applications

For use in diagnostic, research, and therapeutic applications suggested above, kits are also provided by the invention. In the diagnostic and research applications such kits may include any or all of the following: assay reagents, buffers, cytokine biomarker-specific nucleic acids or antibodies, hybridization probes and/or primers.

In some embodiments, the kits of the present invention include selective binding partners for two of the four cytokine biomarkers of the present invention including IL-6. In some embodiments, the kits of the present invention include selective binding partners for three of the four cytokine biomarkers of the present invention, including IL-6. In some embodiments, the kits of the present invention include selective binding partners for two of the four cytokine biomarkers of the present invention including MCP-1. In some embodiments, the kits of the present invention include selective binding partners for three of the four cytokine biomarkers of the present invention, including MCP-1. In some embodiments, the kit contains all four of the cytokine biomarkers.

In some embodiments, the kits of the present invention include the selective binding partners on a continuous solid surface. In such embodiments, the detection of presence or level of all the cytokine biomarkers can be assessed simultaneously. In some embodiments, the binding partners for the cytokine biomarkers of the present invention are present on individual solid surfaces. In such embodiments the presence and level of the cytokine biomarkers can be detected simultaneously or sequentially.

In some kits, the selective binding partners are antibodies to two or more of the cytokines: IL-6, MIP1β, IFNγ or MCP1. In such kits, detection of the presence or level of the cytokine biomarker is by immunoassay. In some embodiments, the kits include primers specific to amplifying any two or more of the four cytokine biomarkers of the present invention. Those of skill in the art can easily determine how to design primers specific for amplifying a particular cytokine biomarker based on the biomarker nucleotide sequence. Nucleotide detection methods can be used with kits comprising primers. In some embodiments, polymerase chain reactions are used to detect the cytokine biomarkers. In some embodiments, the polymerase chain reaction is RT-PCR.

In some kits, a device to be utilized for the extraction of the biological sample is also included in the kit. In some embodiments, the extraction device, e.g., a syringe and a needle, can directly extract the biological sample from the potentially affected joint into a chamber containing the selective binding partners for the cytokine biomarkers. In some instances, the kit, thus allows for immediate assessment of the cytokine biomarkers' presence and/or level and, therefore, immediate diagnosis of a patient suffering from non-immune inflammatory acute joint injury. These types of kits are particularly suitable for use at the point of care. An example of a point of care diagnostic system is described in U.S. Pat. No. 6,267,722 which is incorporated herein by reference. Other devices whose design can be adapted for use with the kits of the present invention are described, for example, in U.S. Pat. Nos. 7,198,522 and 6,818,455.

In some embodiments, the potentially affected joint does not contain sufficient fluid for extraction. Thus, in some embodiment, a lavage of the potentially acutely injured joint is necessary. In such embodiments, the kit may include a solution to be used for the extraction of the biological sample from the joint. This solution included in the kit can be, for example, a physiologic solution, e.g. saline.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

VIII. EXAMPLES

Example 1

Subjects and Knee Lavage

This prospective, cohort study was approved by the Institutional Review Boards of Parkway Regional Medical Center and the University of Miami, Jackson Memorial Medical Center. Forty-three subjects were enrolled in the study after providing their informed consent. Between the dates of July 2006 and June 2007, patients were selected from a cohort of approximately 200 patients referred for the evaluation of knee pain to two board-certified orthopaedic surgeons, fellowship-trained in sports medicine. All patients underwent a routine focused physical examination and a Magnetic Resonance Imaging (MRI) of the knee. MRI scans were read and interpreted by a single, independent, board-certified radiologist. Patients were asked to rate the pain in both knees on a 0-10 visual analog scale (VAS). Patients deemed appropriate to undergo arthroscopic surgery as part of their treatment were asked to participate in the study. Not all patients who participated in the study consented to aspiration of the contralateral asymptomatic knee. Upon induction of general anesthesia, synovial fluid aspiration was obtained via lavage in the operative knee or both knees utilizing approximately 10-20 ml of sterile physiologic saline, allowing the withdrawal of 2-3 ml of lavasate. The lavasate was then placed into 2 ml microfuge tubes containing 130 ul of protease inhibitor cocktail tablets (Roche Diagnostics, Indianapolis, Ind.) dissolved in PBS (0.045 tablet/ml sample) and frozen at −20° C. temporarily until being shipped to Stanford University on dry ice where samples were subsequently alliquoted and stored at 80° C. Intraoperative findings were cataloged and chondral defects graded using the Outerbridge classification. Patients repeated VAS pain ratings of both knees 3 months post-operatively.

In addition to the surgical group, 14 volunteers were enrolled in the study after consent was obtained for lavage of a knee without previous or current injury or pain and with no surgical history. Individuals underwent office-based knee lavage. The skin was sterilized with Betadine solution and anesthetized with a topical anesthetic, and the knee lavage was performed as described above for intra-operative lavages.

The orthopaedic surgeons performing the knee lavages and surgeries, as well as the radiologist, completed all aspects of the study in a manner blinded to the assay procedure and results.

Example 2

Inclusion and Exclusion Criteria

Inclusion criteria: Patients 18-80 years old presenting with symptoms of knee pain, either secondary to arthritis or a traumatic event and who satisfied clinical indications for arthroscopic surgery following MRI of the symptomatic knee.

Exclusion criteria: less than 18 years old, recent (within 3 months) intra-articular corticosteroid injection, past or current medical history of autoimmune disease. In addition, no patients involved in a worker's compensation claim or personal injury litigation, were enrolled in the study.

Example 3

Cytokine Analysis

The concentrations of 17 inflammatory cytokines and chemokines (IFNγ, IL-2, IL-4, IL-5, IL-6, IL-7, IL-8, IL-10, IL-12, IL-13, IL-17, G-CSF, GM-CSF, TNFα, IL-1β, MCP-1 and MIP-1β) were quantified in knee lavage samples using the human 17-plex inflammatory cytokine panel and the Bio-Plex 200 System (Bio-Rad, Hercules, Calif.), following the manufacture's protocol in a 96-well plate format. This assay utilized a sandwich ELISA linked to polystyrene beads and fluorophores, and has been validated against standard ELISAs of human blood samples (de Jager et al. 2003).

Example 4

Patient Pain Scores, Age and Gender Profile by Group-knee Samples

The mean (±SEM) self-reported visual analog score (VAS) for the normal control group, operative knee group and non-operative knee group was 0±0, 1.6±0.4 and 6.4±0.2, respectively. The mean age of the normal control group, operative knee group and non-operative knee group was 45.7±1.7, 51.5±2.9 and 52.1±3.3 years, respectively. The ratio of male: female of the normal control group, operative knee group and non-operative knee group was 8:6, 26:9 and 18:8, respectively.

The following was observed 1) statistically greater mean intra-articular cytokine concentrations of IL-6, MCP-1, MIP-1β and IFNγ in the operative knee group as compared to the non-operative and normal knee groups; 2) a statistically significant correlation between IL-6 and VAS ratings across all three groups and MCP-1 and VAS ratings across all three groups; 3) a statistically significant correlation between MCP-1 and IL-6 intra-articular concentrations.

TABLE 1 illustrates levels of cytokines from a cohort of normal patients whose knees were not painful.

| Patient Code | AGE | VAS | IFN-gamma* | IL-6* | MCP-1* | MIP-1b* |
|---|---|---|---|---|---|---|
| 964NC | 37 | 0 | 0 | 0.01 | 0 | 0.29 |
| 963NC | 30 | 0 | 0 | 0.01 | 0 | 0.17 |
| 962NC | 31 | 0 | 106.81 | 0.02 | 5.2 | 3.64 |
| 961NC | 40 | 0 | 0 | 0.01 | 0 | 0.21 |
| 960NC | 44 | 0 | 0 | 0.01 | 0 | 0.01 |
| B204 | 37 | 0 | 0 | 0 | 0 | 0 |
| B201 | 44 | 0 | 0 | 0 | 0 | 0 |
| B203 | 32 | 0 | 0 | 0 | 0 | 0 |
| B207 | 45 | 0 | 0 | 0 | 0 | 0 |
| 1039 | 45 | 0 | 29.22 | 0 | 0 | 0.36 |
| 604A | 59 | 0 | 0 | 0 | 0 | 0 |
| 4017A | 69 | 0 | 196.92 | 0 | 38.01 | 0 |
| 789-A | 55 | 0 | 0 | 0 | 0 | 92.6 |
| 950A | 29 | 0 | 9.06 | 0.07 | 0.38 | 1.35 |
| 900A | 19 | 0 | 0 | 0.02 | 0 | 0.24 |
| 967A | 63 | 0 | 0 | 0 | 0 | 0 |
| 660A | 58 | 0 | 0 | 0 | 2.29 | 0 |
| 957A | 67 | 0 | 0 | 0 | 0 | 1.11 |
| B236 | 32 | 0 | 0 | 0 | 0 | 0 |
| B256 | 66 | 0 | 0 | 0 | 0 | 0 |
| B257 | 68 | 0 | 0 | 0 | 2.56 | 0.4 |

*levels are expressed in pg/ml

TABLE 2 illustrates cytokine biomarker levels from patients who experienced various levels of pain (as indicated by the VAS score) in their knee and were selected as candidates for surgery

| Patient Code | AGE | VAS | IFN-gamma* | IL-6* | MCP-1* | MIP-1b* |
|---|---|---|---|---|---|---|
| 326S | 53 | 4 | 891.7 | 76.1 | 41.8 | 13.7 |
| 789S | 55 | 5 | 2835.8 | 0 | 0 | 19.2 |
| B250 | 63 | 6 | 286.7 | 0 | 44.5 | 10.3 |
| 4010 | 50 | 6 | 77.5 | 508.5 | 73.3 | 12.6 |
| 900S | 19 | 6 | 5001.2 | 719.4 | 93.6 | 56.2 |
| 80S | 49 | 6 | 1553.3 | 7.75 | 19.8 | 86.4 |

TABLE 2-continued illustrates cytokine biomarker levels from patients who experienced various levels of pain (as indicated by the VAS score) in their knee and were selected as candidates for surgery

| Patient Code | AGE | VAS | IFN-gamma* | IL-6* | MCP-1* | MIP-1b* |
|---|---|---|---|---|---|---|
| 329RS | 44 | 6 | 530 | 12.1 | 25.1 | 14.4 |
| 302S | 51 | 6 | 1460.9 | 143.9 | 19.6 | 39.8 |
| 4015 | 61 | 6 | 290.6 | 28.4 | 80.9 | 4.7 |
| 953S | 37 | 6 | 4182.7 | 26.4 | 2.5 | 42.9 |
| 955S | 20 | 6 | 62.0 | 14.5 | 9.2 | 1.4 |
| 888S | 61 | 7 | 457.4 | 40.25 | 442.1 | 17.4 |
| 603S | 59 | 7 | 1634.5 | 513.3 | 43.8 | 36.5 |
| 4009S | 57 | 7 | 0 | 120.6 | 93.0 | 15.4 |
| 660S | 58 | 7 | 1105.2 | 96.1 | 63.2 | 44.2 |
| 888S | 61 | 7 | 457.4 | 40.3 | 442.1 | 17.4 |
| 4011S | 56 | 7 | 7.62 | 65.9 | 119.9 | 51.4 |
| 406S | 67 | 7 | 3952.5 | 0 | 10.7 | 47.3 |
| 950S | 29 | 7 | 24259.6 | 1456.9 | 3000 | 871.4 |
| 4013S | 77 | 8 | 5645.7 | 6.0 | 39.4 | 127.7 |
| 4017S | 69 | 8 | 2669.6 | 1399.2 | 3000 | 149.1 |
| 312S | 71 | 10 | 0 | 10.6 | 44.0 | 0 |

*units are expressed in pg/ml
**indicates a patient with previous surgery in the same knee Example 5

Patient Pain Scores, Age and Gender Profile by Group-shoulder Samples

Patient B209 had a traumatic shoulder dislocation with a large effusion. The joint was aspirated and synovial fluid was removed for analysis. The sample was handled in the same manner as the knee samples described above. Patient 312 had a rotator cuff injury with a cartilage lesion of the labrum, called a SLAP lesion. The joint could not be aspirated, so approximately 20 cc of normal saline was injected into the shoulder. The lavage procedure was performed similarly to the ravages described for the normal knees.

TABLE 3 analysis of cytokine biomarker levels in shoulder samples

| Patient Code | AGE | VAS | IFN-gamma* | IL-6* | MCP-1* | MIP-1b* |
|---|---|---|---|---|---|---|
| B209 | 21 | 6 | 1060 | 71.05 | 174.7 | 30.44 |
| B312 | 31 | 5 | 0 | 10.59 | 44.06 | 0 |

*units are in pg/ml

Example 6

Using IL-6 as Optimal Specificity Biomarker of Acute Joint Injury

The results of the analysis are summarized in Table 4. The assay involving IL-6 alone has optimal specificity, but suboptimal sensitivity and accuracy. The addition of MCP-1 to IL-6 increases sensitivity at the cost of decreasing specificity, but has the best overall accuracy. The further addition of MIP-1β trades a small decrease in specificity for a small increase in sensitivity, and yields slightly lower overall accuracy. But the analysis of all four cytokines together yields the best overall accuracy, high specificity and improved sensitivity over other options. The model with four cytokines achieves the goal of specificity of approximately 95% or greater, sensitivity of 80% or greater, and overall accuracy of 90% or greater.

The statistical method used was binary logistic regression with backward stepwise model building using a Wald statistic. The classification cutoff was 0.5, and the probability for stepwise removal was 0.1. First order effects were considered, and a constant was included. The addition of second order effects did not change the results.

TABLE 4

A comparison of the sensitivity, specificity and accuracy of immunoassays with various analytes. The cross (X) indicates that the analyte was used in the assay.

| IL-6 | IFN-g* | MIP-1b* | MCP-1* | Sensitivity | Specificity | Accuracy |
|---|---|---|---|---|---|---|
| X | | | | 69.6 | 100 | 83.3 |
| X | X | | | 78.3 | 100 | 88.1 |
| X | X | X | | 78.3 | 100 | 88.1 |
| X | X | | X | 82.6 | 94.7 | 88.1 |
| X | X | X | X | 87.0 | 94.7 | 90.5 |

*levels are expressed in pg/ml

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications and accession numbers cited herein are hereby incorporated by reference.

What is claimed is:

1. A method of selecting a patient for treatment, wherein the patient has non-autoimmune acute pain of a joint, the method comprising:
    detecting the level of IL-6 and at least one other cytokine selected from the group consisting of MCP-1, MIP-1β and IFNγ relative to levels in synovial fluid from a joint in a normal individual, wherein a detectable level of IL-6 greater than 0.07 pg/ml and the at least one other cytokine is indicative of a patient to be selected for treatment.

2. The method of claim 1, further comprising detecting the level in of at least one additional other cytokine selected from the group consisting of MCP-1, MIP-1β and IFNγ in the synovial fluid from the joint.

3. The method of claim 1, wherein the synovial fluid is a fluid from the joint or a joint lavage sample.

4. The method of claim 1, wherein the method of detection comprises an immunoassay.

5. The method of claim 1, wherein the joint is selected from the group consisting of knee, wrist, ankle, elbow, hip and shoulder.

6. The method of claim 1, further comprising administering an anti-inflammatory agent to the patient, wherein the anti-inflammatory agent is an inhibitor of IL-6, MCP-1, MIP-1β, or IFNγ.

7. The method of claim 6, wherein the inhibitor is an antibody.

8. The method of claim 1 comprising: detecting the level of MCP-1 in synovial fluid.

* * * * *